United States Patent
Majeti et al.

(10) Patent No.: US 7,025,950 B2
(45) Date of Patent: *Apr. 11, 2006

(54) ORAL CARE COMPOSITIONS COMPRISING DICARBOXY FUNCTIONALIZED POLYORGANOSILOXANES

(75) Inventors: Satyanarayana Majeti, Middletown, OH (US); Elizabeth Ann Brown Reno, Fairfield, OH (US); Stephen Andras Kovacs, Loveland, OH (US); William Michael Glandorf, Mason, OH (US); Philippe Olier, Lyons (FR)

(73) Assignee: The Procter & Gamble Company, Cincinnati, OH (US)

( * ) Notice: Subject to any disclaimer, the term of this patent is extended or adjusted under 35 U.S.C. 154(b) by 119 days.

This patent is subject to a terminal disclaimer.

(21) Appl. No.: 10/430,617

(22) Filed: May 6, 2003

(65) Prior Publication Data
US 2003/0211051 A1    Nov. 13, 2003

Related U.S. Application Data

(60) Provisional application No. 60/378,994, filed on May 9, 2002.

(51) Int. Cl.
*A61K 7/16* (2006.01)

(52) U.S. Cl. .................... 424/49; 424/50; 424/52; 424/53; 528/25; 528/26; 528/31

(58) Field of Classification Search .................. 424/49; 528/26, 29; 556/439
See application file for complete search history.

(56) References Cited

U.S. PATENT DOCUMENTS

| | | | |
|---|---|---|---|
| 4,207,246 A * | 6/1980 | Hafner et al. ............... | 556/439 |
| 4,342,742 A | 8/1982 | Sebag et al. | |
| 4,501,619 A | 2/1985 | Gee | |
| 4,563,347 A | 1/1986 | Starch | |
| 4,587,320 A | 5/1986 | Swihart | |
| 4,658,049 A | 4/1987 | Nakano et al. | |
| 4,701,269 A | 10/1987 | Bay et al. | |
| 4,844,888 A | 7/1989 | Zawadzki | |
| 4,857,212 A | 8/1989 | Ona et al. | |
| 4,876,152 A | 10/1989 | Kang | |
| 4,931,062 A | 6/1990 | Bay et al. | |
| 4,944,978 A | 7/1990 | Pipkins | |
| 5,015,700 A | 5/1991 | Herzig et al. | |
| 5,032,387 A | 7/1991 | Hill et al. | |
| 5,057,308 A | 10/1991 | Hill et al. | |
| 5,063,044 A | 11/1991 | Kohl et al. | |
| 5,063,052 A * | 11/1991 | Grollier et al. ........ | 424/70.121 |
| 5,078,988 A | 1/1992 | Lin et al. | |
| 5,087,443 A * | 2/1992 | Chizat et al. ................. | 424/47 |
| 5,154,915 A | 10/1992 | Weber et al. | |
| 5,165,913 A | 11/1992 | Hill et al. | |
| 5,188,822 A | 2/1993 | Viccaro et al. | |
| 5,210,251 A | 5/1993 | Ohashi et al. | |
| 5,248,783 A | 9/1993 | O'Lenick | |
| 5,280,019 A | 1/1994 | Klimisch | |
| 5,296,625 A | 3/1994 | O'Lenick, Jr. et al. | |
| 5,422,098 A | 6/1995 | Rolla et al. | |
| 5,427,770 A | 6/1995 | Viccaro et al. | |
| 5,504,233 A | 4/1996 | Bindl et al. | |
| 5,536,304 A | 7/1996 | Coppens et al. | |
| 5,702,490 A | 12/1997 | Kneip et al. | |
| 5,759,523 A | 6/1998 | Hughes et al. | |
| 5,827,505 A | 10/1998 | Hughes et al. | |
| 5,856,282 A | 1/1999 | Hughes | |
| 5,888,491 A | 3/1999 | Mitra et al. | |
| 6,004,538 A | 12/1999 | Hughes et al. | |
| 6,007,801 A | 12/1999 | Hossel et al. | |
| 6,024,891 A | 2/2000 | Hughes | |
| 6,129,906 A | 10/2000 | Steventon | |
| 6,153,567 A | 11/2000 | Hughes | |
| 6,743,884 B1 * | 6/2004 | Olier ........................... | 528/26 |

FOREIGN PATENT DOCUMENTS

| | | |
|---|---|---|
| JP | 04/120014 | 4/1992 |
| JP | 5-331291 | * 12/1993 |

* cited by examiner

*Primary Examiner*—Marc S Zimmer
(74) *Attorney, Agent, or Firm*—Emelyn L. Hiland

(57) ABSTRACT

Disclosed are compositions and methods for treating and modifying surfaces and for enhancing delivery of active agents to surfaces treated with the compositions, which comprise siloxane polymers functionalized with pendant moieties comprising anionic groups, specifically carboxylic acid groups. When applied to a suitable surface, the present composition comprising the carboxy functionalized siloxane polymers forms a substantially hydrophobic coating on the treated surface. These polymers effectively deposit on surfaces that have cationic sites, which are capable of forming bonds or linkages with the anionic groups of the polymer. The treated surface becomes hydrophobic due to the deposition of the carboxy functionalized siloxane polymer, which then imparts a variety of end use benefits to that surface such as ease of cleaning, stain removal and prevention, whitening, etc. The carboxy functionalized siloxane polymer further acts as a carrier to deposit active agents onto the surface and to improve retention and efficacy of said actives on the treated surface. The present compositions are useful in a variety of applications including oral care, hair and skin care, personal care, cosmetics, and fabric and hard surface cleaning and conditioning. Examples are oral compositions for use in cleaning and whitening of natural teeth and dental prosthesis; for preventing, reducing or removing plaque, calculus and surface deposited stains on teeth; and for providing shine, smoothness and positive feel benefits to teeth, the compositions comprising at least about 0.1% by weight of a dicarboxy functionalized siloxane polymer in a formulation that effectively deposits the polymer to teeth and other oral surfaces.

7 Claims, No Drawings

ORAL CARE COMPOSITIONS COMPRISING DICARBOXY FUNCTIONALIZED POLYORGANOSILOXANES

CROSS REFERENCE TO RELATED APPLICATIONS

This application claims the benefit of U.S. Provisional Application No. 60/378,994, filed May 9, 2002.

FIELD OF THE INVENTION

This invention provides compositions and methods for treating and modifying surfaces and for enhancing delivery of active agents to surfaces treated with the compositions which comprise siloxane polymers functionalized with pendant moieties comprising anionic groups, specifically carboxy groups. When applied to a suitable surface, the present composition comprising the carboxy functionalized siloxane polymers forms a substantially hydrophobic coating on the treated surface. These polymers effectively deposit on surfaces that have cationic sites, which are capable of forming bonds or linkages with the anionic groups of the polymer. The treated surface becomes hydrophobic due to the deposition of the carboxy functionalized siloxane polymer, which then imparts a variety of end use benefits to that surface such as ease of cleaning, stain removal and prevention, whitening, etc. The carboxy functionalized siloxane polymer further acts to enhance deposition of active agents onto the surface and to improve retention and efficacy of these actives on the treated surface. The present compositions are useful in a variety of applications including oral care, hair and skin care, personal care, cosmetics, and fabric and hard surface cleaning and conditioning.

BACKGROUND OF THE INVENTION

It is desirable to have a means to modify surfaces in order to impart properties to such surfaces including ease of cleaning; resistance to soiling, staining and adherence of bacteria and other unwanted deposits; water repellency; as well as appearance and textural benefits including whitening, glossiness, softness, smoothness and lubricity. While the art is replete with a myriad of products aimed at providing one or more of these benefits, there continues to be a search for improved means to deliver these benefits.

In particular, modifying surfaces to be hydrophobic, is advantageous in providing the aforementioned benefits. For example, hydrophobic surfaces tend to repel most soils and stains and would thus be easier to clean. Surfaces such as fabrics, ceramics, porcelain, glass and teeth can be hydrophobically modified for ease of cleaning and anti-staining benefits. A hydrophobic coating on fabrics, paper, leather, skin and hair would also provide desirable textural characteristics including softness, smoothness and lubricity.

Silicone oils including the polyalkylsiloxanes such as polydimethylsiloxanes (PDMS), because of their hydrophobic nature, have been suggested for inclusion for example in oral hygiene preparations to inhibit the adhesion of food particles, cellular debris and plaque precursors to teeth such as described in U.S. Pat. Nos. 5,032,387; 5,165,913; 5,057,308 all to Hill, et al. U.S. Pat. No. 5,422,098 to Rolla et al. discloses dentifrices comprising a liquid silicone oil, such as PDMS, and a fat-soluble antibacterial agent dissolved therein, which is described as being useful for protection of teeth against plaque formation due to a slow release of antibacterial agent into the saliva. However, PDMS polymers have not generally been used successfully for coating the teeth because of poor adhesion and retention of the PDMS on tooth surfaces. To improve the adherence of the silicone on surfaces, it has been suggested to modify the silicone by addition of functional groups such as carboxy, anhydride, polyol and amino groups. Such modified silicones have been suggested for modifying various surfaces; including fibers, textiles, leather, hair and skin, teeth, paper, plastic, wood, metal, glass, stone and concrete. For example, aminoalkyl silicones are described in U.S. Pat. Nos. 5,078,988; 5,154,915; 5,188,822; and 5,427,770, all assigned to Chesebrough-Ponds and in U.S. Pat. Nos. 6,153,567; 6,129,906 and 6,024,891, all assigned to Procter & Gamble. Carboxyl or anhydride group containing silicones are disclosed in U.S. Pat. Nos. 4,501,619; 4,563,347; 4,587,320; 4,944,978; 5,063,044 5,280,019, all assigned to Dow Corning; in U.S. Pat. No. 4,857,212 assigned to Toray Silicone; U.S. Pat. Nos. 4,701,269; 4,931,062; 5,702,490 and 6,007,801, all assigned to BASF; U.S. Pat. No. 4,658,049 assigned to Chisso; U.S. Pat. No. 4,844,888 assigned to Gillette; U.S. Pat. Nos. 5,248,783 and 5,296,625 both assigned to Siltech; U.S. Pat. Nos. 5,015,700 and 5,504,233 assigned to Wacker Chemie; JP Patent Publication No. 04/120014 and U.S. Pat. No. 5,210,251 assigned to Kao; U.S. Pat. No. 4,876,152 assigned to PPG; U.S. Pat. No. 4,342,742 assigned to L'Oreal and U.S. Pat. Nos. 5,536,304 and 5,888,491, both assigned to 3M. Dimethicone copolyols are disclosed in U.S. Pat. Nos. 5,759,523; 5,827,505; 5,856,282; 6,004,538 and 6,129,906 all assigned to Procter & Gamble.

Even with the substantial body of work in this area, there continues to be a search for substantive polymers that can be deposited onto surfaces to modify the characteristics of these surfaces thereby providing a variety of the aforementioned benefits thereon. The present invention thus provides surface modifying substantive siloxane polymers and compositions comprising these polymers, which find utility, for example, in applications for the care of teeth and other surfaces of the oral cavity.

Human teeth are constructed with an inner soft layer called dentin and an outer hard layer called enamel that protects the inner structure. The enamel layer of teeth is naturally a translucent white or slightly off-white color. Under typical conditions, the enamel surface is coated with a thin layer of salivary proteins called pellicle. Either the enamel or pellicle or both can be discolored or stained and present to the outside an undesirable appearance. Further, the enamel layer of teeth is largely made of hydroxyapatite mineral crystals that create a porous surface structure. It is believed that the porous nature of enamel is what allows staining components and discoloring substances to penetrate into the tooth structure making it appear stained. Tooth discoloration is either extrinsic, on the enamel/pellicle, or intrinsic, penetrating the enamel and dentin or both.

Effective cleaning of the oral cavity to ensure oral cavity health requires control of dental plaque and calculus. The formation of dental plaque and calculus is the primary source of dental caries, gingivitis, periodontal disease, and tooth loss. Dental plaque is a mixed matrix of bacteria, epithelial cells, leukocytes, macrophages and other oral exudate. Bacteria comprise approximately three-quarters of the plaque matrix. Any given sample of dental plaque could contain as many as 400 different varieties of microorganisms. This mix includes both aerobic and anaerobic bacteria, fungi, and protozoa. Viruses have also been found in samples of dental plaque.

This matrix of organisms and oral exudate continues expanding and coalesces with other plaque growths situated nearby. The bacteria synthesize levans and glucans from sucrose found in the oral cavity providing energy for the microorganisms. These glucans, levans, and microorganisms form an adhesive skeleton for the continued proliferation of plaque.

Plaque, in turn, acts as a nucleus for the formation of calculus. Dental calculus or tartar as it is sometimes called, is a deposit, which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars. Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms. Developing plaque can also adhere most easily at relatively irregular surfaces, such as those afforded by calculus. As calculus matures and hardens, it becomes visibly white or yellowish in color unless stained or discolored due to the absorption of dietary chromagens. In addition to being unsightly and undesirable from an aesthetic standpoint, the mature calculus deposits are constant sources of irritation of the gingiva.

The failure to retard or stop the proliferation of plaque and calculus is detrimental to oral health. Plaque and calculus formation may lead to dental caries, gingival inflammation, periodontal disease, and ultimately tooth loss. Additionally, calculus and plaque along with behavioral and environmental factors lead to formation of dental stains, significantly affecting the aesthetic appearance of teeth. Behavioral and environmental factors that contribute to teeth staining propensity include regular use of coffee, tea, cola or tobacco products, and also the use of stain promoting oral products, such as chlorhexidine.

The present compositions comprising specific carboxy functionalized siloxane polymers provide antiplaque, anticalculus and antistain benefits by depositing a hydrophobic coating on teeth, the hydrophobic coating being retained thereon for a sufficient period of time to provide resistance to soiling, staining and adherence of bacteria and other unwanted deposits. In addition, the present compositions provide enhanced delivery and retention of oral care actives such as bleaching agents to tooth surfaces, and thus, improved whitening and stain removal.

SUMMARY OF THE INVENTION

The present invention provides oral compositions for use in cleaning and whitening of natural teeth and dental prosthesis and for preventing, reducing or removing plaque, calculus and surface deposited stains on teeth, the compositions comprising at least about 0.1% by weight of a carboxy functionalized siloxane polymer in a formulation that effectively deposits the polymer to teeth and other oral surfaces, forming a substantive coating having prolonged retention thereon. The present polymers comprise a hydrophobic siloxane backbone having pendant moieties containing carboxy groups, and have the ability to deposit onto polar surfaces, i.e., having cationic sites. The compositions may be aqueous or essentially non-aqueous based and may further comprise one or more oral care actives such as teeth whitening agents including bleaches and color modifying agents, antimicrobials, enzymes, fluoride, desensitizing agents, and flavors. This invention further relates to methods of cleaning and whitening natural teeth and dental prosthesis; preventing, reducing or removing plaque, caries, tartar, and surface deposited tooth stains; and providing shine, smoothness and positive tooth feel benefits by administering the present compositions.

These and other features, aspects, and advantages of the present invention will become evident to those skilled in the art from the following detailed description.

DETAILED DESCRIPTION OF THE INVENTION

While the specification concludes with claims, which particularly point out and distinctly claim the invention, it is believed the present invention will be better understood from the following description.

All percentages and ratios used herein are by weight of the specific oral composition and not of the overall oral formulation that is delivered, unless otherwise specified. All measurements are made at 25° C., unless otherwise specified.

Herein, "comprising" means that other steps and other ingredients which do not affect the end result can be added. This term encompasses the terms "consisting of" and "consisting essentially of".

By "oral composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition of the present invention may be in the form of a toothpaste, dentifrice, tooth powder, tooth gel, subgingival gel, mouthrinse, denture product, mouthspray, lozenge, oral tablet, or chewing gum. The oral composition may also be incorporated onto strips or films for direct application or attachment to oral surfaces.

The term "dentifrice", as used herein, means paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "orally acceptable carrier" as used herein means any safe and effective materials for use in the compositions of the present invention. Such materials include fluoride ion sources, anticalculus agents, buffers, abrasive polishing materials, peroxide sources, alkali metal bicarbonate salts, thickening materials, humectants, water, surfactants, titanium dioxide, flavor system, sweetening agents, xylitol, coloring agents, and mixtures thereof.

Herein, the terms "tartar" and "calculus" are used interchangeably and refer to mineralized dental plaque deposits.

In accordance with the present invention, compositions are provided that comprise as an essential ingredient at least one siloxane polymer functionalized with carboxylic acid groups, for application to polar surfaces such as teeth, ceramics, skin, fabrics, hair, glass and paper. The compositions comprise at least about 0.1% of the carboxy functionalized siloxane polymer in a formulation that effectively deposits the polymer to the treated surface. The present polymers comprise a hydrophobic siloxane backbone and pendant anionic moieties containing carboxy groups and have the ability to deposit onto surfaces from aqueous-based formulations such as cleaning and detergent compositions and from essentially non-aqueous based formulations. When applied to a suitable surface, the present composition comprising the carboxy functionalized siloxane polymers forms a substantially hydrophobic coating on the treated surface, the coating having prolonged retention thereon.

The carboxy functionalized siloxane polymers useful in the present invention are believed to attach themselves to polar surfaces and to form a coating thereon by electrostatic interaction, i.e., complex formation between the pendant carboxy groups of the polymer with cations or some other positively charged sites on the treated surface. For example, in the case of oral application it is believed the carboxy groups will interact with the calcium ions present in teeth. In the case of fabrics, the interaction may be with calcium ions or cellulose groups; in the case of hair or skin, with the protein residues; in the case of glass or ceramics, with calcium and other metal ions. The carboxy groups thus serve to anchor the siloxane polymer backbone onto a surface thereby modifying it to be hydrophobic.

Preferably, the functional group pendant from the polysiloxane main chain comprises two carboxy groups, resulting in improved deposition and retention of the polymer particularly on surfaces such as teeth that contain positively charged calcium ions. The interaction between the carboxy groups and the tooth surface is electrostatic in nature in which the anionic carboxy groups form a complex with the positively charged calcium ions.

Dicarboxy acid functionalized polyorganosiloxanes useful in the present invention have the formula

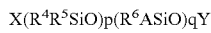

wherein the X end group represents a triorganosiloxyl end group of formula $R^1R^2R^3SiO-$, or a Z end group wherein Z represents —OH;

the Y end group represents a triorganosilyl end group of formula $-SiR^3R^2R^1$ or a W end group wherein W represents —H;

$R^1$ to $R^6$, which may be identical or different, each represents a linear or branched C1–C8 alkyl or phenyl radical, preferably methyl;

A represents a dicarboxy acid radical of formula

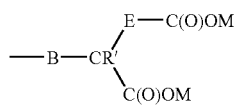

wherein

B represents an alkylene residue having from 2 to 30 carbon atoms, preferably from 3 to 8 carbon atoms, optionally substituted by one or more alkyl radicals having from 1 to 30 carbon atoms, R' represents a hydrogen atom or an alkyl radical having from 1 to 30 carbon atoms, E is nil or is an alkylene residue having from 1 to 5 carbon atoms, preferably from 1 to 3 carbon atoms, optionally substituted by one or more alkyl radicals having from 1 to 30 carbon atoms; and M is H, a cation or an alkyl radical having from 1 to 4 carbon atoms optionally substituted with hydroxy or alkoxy groups;

p is an average value ranging from 0 to 1000, preferably from 0 to 500, more preferably from 5 to 200;

q is an average value ranging from 1 to 100, preferably from 1 to 50; and the ratio of the number of Z and W end groups to the total number of end groups X and Y ranges from 0/100 to 75/100, preferably from 0/100 to 30/100.

In a preferred embodiment, the p/q ratio is from 1/3 to 99/1 (corresponding to 1–75% of pendant diacid groups relative to the siloxyl units), preferably from 1/1 to 10/1. The products where Z is —OH and/or Y is H, are by-products.

The cation salts of the dicarboxy radical can be alkali metal (sodium, potassium, lithium) salts, alkaline earth metal (calcium, barium) salts, non-substituted or substituted ammonium (methyl-, dimethyl-, trimethyl-, or tetramethylammonium, dimethylpiperidinium) salts or can derive from an alkanolamine (monoethanolamine, diethanolamine, triethanolamine).

In addition to the mono- or diester derivatives of the dicarboxy radical (M=alkyl), the present invention includes the amide and diamide derivatives.

The present dicarboxy functionalized siloxane polymers are generally prepared by a hydrosilylation reaction of a polyalkylhydrogensiloxane and an alpha-olefinic anhydride, the precursor of the dicarboxy A groups, with the aid of an effective amount of a hydrosilylation metal catalyst (platinum), as described for example, in U.S. Pat. Nos. 3,159,601; 3,159,662; and 3,814,730, followed by hydrolysis of the anhydride groups.

The hydrosilylation reaction can be carried out at a temperature from 20 to 200° C., preferably from 60 to 120° C., preferably with the aid of a platinum KARSTEDT catalyst (from 1 to 300 ppm, preferably from 5 to 50 ppm by weight of Pt). The relative quantities of polyalkylhydrogensiloxane and alpha alkenyl anhydride correspond to a stoichiometric excess of alpha alkenyl anhydride (at most 5 moles of alpha alkenyl anhydride per mole of polyalkylhydrogensiloxane, preferably at most 2 moles of alpha alkenyl anhydride per mole of polyalkylhydrogensiloxane.

The hydrolysis reaction can be carried out with water at a temperature ranging from room temperature to 150° C., preferably from 40 to 120° C., with or without catalysts. Suitable catalysts for the reaction can be Lewis acids such as $TiCl_4$, $ZnCl_2$, $MgCl_2$, or Bronstedt acids or bases such as $CH_3COOH$, $H_2SO_4$, HCl, KOH, $NaHCO_3$, in an amount ranging from 0.05 to 5%.

Preferred polymers comprise one or a combination of the following dicarboxy acid pendant groups:

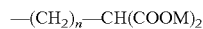

where n is from 2 to 30.

In a preferred embodiment, the diacid pendant group A in the functionalized polyorganosiloxane is $-(CH_2)_3-CH(COOM)-CH_2COOM$ and the polymer is prepared by a hydrosilylation reaction of a polyalkylhydrogensiloxane and allyl succinic anhydride followed by hydrolysis of the anhydride groups. Preferably, the polyalkylhydrogensiloxane is polydimethylhydrogensiloxane and the polymer is terminated with trimethylsilyl groups.

The carboxylic acid groups provide ready bonding/binding to cationic and charged surfaces via electrostatic interaction, hydrogen bonding, or complexation with cations. Such bonding leads to ready deposition of the polymer upon application to form a coating on the treated surface, with charge interaction being the driving force, and at the same time stronger bonding leading to longer retention or durability of the coating. The polysiloxane backbone modifies the surface to be hydrophobic, which imparts properties to the surface including water repellency, faster drying, stain repellency, ease of cleaning, softness and lubricity. Compared to non-functionalized polysiloxanes such as PDMS, the present polymers perform better not only in terms of ease of deposition and retention of the coating, but also in requiring lower levels and in being easier to formulate and emulsify with ordinary surfactants. Even more advantageously, the present polymers have the ability to act as a carrier for other active agents such as for example, teeth whitening agents including bleaches and color modifying agents, antimicrobials, anticaries agents, enzymes, cosmetic ingredients, flavors and fragrances, and can thus act as a highly effective matrix for sustained release of the active agents to the surface where their activity is needed. Another important advantage of the polymer coating is substantivity or the ability to bind or adhere to a surface for a prolonged period of time. Specifically, substantivity relates to the ability of the polymer coating to be retained on the treated surface thereby acting as protective barrier to prevent active agents deposited thereon from being rapidly washed away. Substantivity is important because it allows for prolonged contact of the active agents with the surface being treated. The result is enhancement of the bleaching, antimicrobial, anticaries or other active effect delivered to the surface. The present invention provides oral care compositions that deposit a substantive hydrophobic coating on teeth or other oral surface that is retained for a sufficient period of time to deliver the desired benefit particularly with repeated use.

In particular, with respect to bleach delivery from a daily use oral care composition such as dentifrice or mouthrinse, the present polymers having a hydrophobic polysiloxane backbone and pendant moieties containing dicarboxy groups are uniquely suited to facilitate delivery and retention of the bleaching agent on teeth for a period of time sufficient to provide a noticeable whitening benefit, particularly with repeated use of the compositions. Applicants have found that conventional dentifrices containing bleach are generally ineffective at providing a whitening benefit because the bleach is not retained on teeth for a long enough period. The present method of using a substantive polymer to deposit and retain the bleaching agent for a prolonged contact time thus represents a novel approach.

Notwithstanding the specific polysiloxane structures described herein, it is expected that other hydrophobic polymers suitably functionalized to deposit and adhere to teeth and to facilitate delivery and retention of bleach actives would provide the desired whitening benefit. By "suitably functionalized" is meant that the polymer contains functional groups that would interact with the tooth surface such as by complexation with calcium ions to form a substantive hydrophobic coating thereon. By forming a "substantive hydrophobic coating" on a surface is meant that the hydrophobic character of the surface is increased as measured, for example, by an increase in the water contact angle of the surface of at least about 15 degrees and the increased hydrophobic character is maintained for a period of at least about 5 minutes. For example, the water contact angle of dental enamel after treatment with a composition comprising the present dicarboxy functionalized polysiloxane may increase by about 20 degrees up to about 50 degrees depending on a number of factors including pH, the condition of the oral environment and tooth surface characteristics.

In one aspect the present invention provides oral care compositions for daily use comprising in an orally acceptable carrier at least about 0.1% of a dicarboxy functionalized siloxane polymer that deposit a hydrophobic coating on teeth, which coating is retained for a period of at least about 5 minutes up to about eight hours following each use. The present oral compositions provide enhanced overall cleaning, inhibition of plaque, whitening, stain removal and prevention of staining of natural teeth and dental prosthesis. Without wishing to be limited to a particular mechanism of action, it is believed the carboxy groups of the present functionalized siloxane polymer, complex with the positively charged calcium ions present on the tooth surface. The calcium/polymer complex is particularly stable when the polymer contains at least two carboxy groups to complex with divalent calcium ions forming 5-, 6- and 7-membered ring structures. Such complex formation is the driving force for deposition and retention of the polymer coating onto teeth. It is believed that the polymer coating on the teeth acts as a barrier to prevent staining and plaque formation. Color bodies or staining materials such as polyphenolic compounds (catechols and tannins) are constituents of various dietary products such as tea, coffee, wine, cola, and a variety of fruits and berries. Consumption of these dietary products is known to cause deposition of staining materials on teeth. When the present compositions are applied to the oral cavity such as by toothbrushing or by rinsing, a hydrophobic siloxane polymer coating is deposited onto teeth. Thus when color bodies are introduced in the oral cavity, they contact the siloxane polymer coating instead of the tooth surface, thereby preventing stain from forming on teeth. Freshly formed plaque can also be prevented from forming on teeth and the polymer coating additionally inhibits the ability of plaque to absorb colored components from ingested products such as tea, beer, red wines, etc. and form stain on teeth.

Further, the present dicarboxy functionalized polymers have the ability to act as a carrier for oral care actives such as bleaches and other teeth whitening agents, antimicrobials, fluoride, desensitizing agents, and flavors and to facilitate deposition and retention of these actives onto the oral surfaces where they can perform their intended function. It is believed the polymer coating also acts as a protective barrier that retains the oral care active in close contact with the oral surface thereby ensuring that the activity such as bleaching or antimicrobial effect lasts longer. Effective bleaching will remove stains and lead to whiter teeth. Enhanced retention of antimicrobials on the oral surfaces will result in reducing the oral microorganisms that are causative agents of, or associated with, various dental diseases, including gingivitis, periodontal disease, and dental plaque.

Accordingly in a further aspect of the invention, there is provided a composition for use in overall cleaning, whitening, removing stain and preventing stain build-up on human teeth and dental prosthesis comprising the combination of at least about 0.1% of a carboxy-functionalized siloxane polymer and from about 0.1% to about 20.0% teeth whitening agent, preferably from about 1% to about 10% teeth whitening agent in an orally acceptable carrier.

A suitable copolymer for use in the present invention is a siloxane polymer with propyl succinic acid pendant groups and having an average molecular weight (AMW) ranging from about 300 to about 300,000 available from Rhodia. Preferred polymers are those with an average molecular weight ranging from 1000 to 100,000 and having from about 1% to 75% of pendant diacid groups relative to the siloxyl units. The polymer is incorporated in the present dentifrice, rinse, chewing gum and the like compositions at about 0.1% to about 20% by weight, preferably from about 0.5% to about 5% by weight. Greater amounts up to about 80% may be used for oral gels such as paint-on or leave-on gels or for denture adhesives.

Teeth whitening actives that may be used in the oral care compositions of the present invention include bleaching or oxidizing agents such as peroxides, perborates, percarbonates, peroxyacids, persulfates, metal chlorites, and combinations thereof. Suitable peroxide compounds include hydrogen peroxide, urea peroxide, calcium peroxide, and mixtures thereof. A preferred percarbonate is sodium percarbonate. Other suitable whitening agents include potassium, ammonium, sodium and lithium persulfates and perborate mono- and tetrahydrates, and sodium pyrophosphate peroxyhydrate. Suitable metal chlorites include calcium chlorite, barium chlorite, magnesium chlorite, lithium chlorite, sodium chlorite, and potassium chlorite. The preferred chlorite is sodium chlorite. Additional whitening actives may be hypochlorite and chlorine dioxide.

The oral composition of the present invention may be in the form of a dentifrice, toothpaste, tooth powder, topical oral gel, mouthrinse, denture product, mouthspray, lozenge, oral tablet, or chewing gum. The oral composition may also be incorporated onto strips or films for direct application or attachment to oral surfaces.

The present oral care compositions in aqueous form will optimally have a pH ranging from about 4.0 to about 10.0. Preferred pH of the compositions is from about 5.0 to about 8.0.

In addition to the components described above, the present oral care compositions may comprise additional components, which are described in the following paragraphs.

Orally Acceptable Carrier

The orally acceptable carrier comprises one or more compatible solid or liquid filler diluents or encapsulating substances, which are suitable for topical oral administration. By "compatible," as used herein, is meant that the components of the composition are capable of being commingled without interaction in a manner which would substantially reduce the composition's stability and/or efficacy.

The carriers or excipients of the present invention can include the usual and conventional components of dentifrices (including non-abrasive gels and gels for subgingival application), mouth rinses, mouth sprays, chewing gums, and lozenges (including breath mints) as more fully described hereinafter.

The choice of a carrier to be used is basically determined by the way the composition is to be introduced into the oral cavity. If a toothpaste (including tooth gels, etc.) is to be used, then a "toothpaste carrier" is chosen (comprising e.g., abrasive materials, sudsing agents, binders, humectants, flavoring and sweetening agents, etc.) as disclosed in e.g., U.S. Pat. No. 3,988,433, to Benedict. If a mouth rinse is to be used, then a "mouth rinse carrier" is chosen (comprising e.g., water, flavoring and sweetening agents, etc.), as disclosed in e.g., U.S. Pat. No. 3,988,433 to Benedict. Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al.; if a chewing gum is to be used, a "chewing gum carrier" is chosen (comprising e.g., gum base, flavoring and sweetening agents), as disclosed in e.g., U.S. Pat. No. 4,083,955, to Grabenstetter et al. If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g., U.S. Pat. No. 5,198,220, issued Mar. 30, 1993 and U.S. Pat. No. 5,242,910, issued Sep. 7, 1993, both to Damani. Other useful carriers include biphasic dentifrice formulations such as those disclosed in U.S. Pat. No. 5,213,790, issued May 23, 1993, U.S. Pat. No. 5,145,666, issued Sep. 8, 1992, and U.S. Pat. No. 5,281,410 issued Jan. 25, 1994 all to Lukacovic et al. and in U.S. Pat. Nos. 4,849,213 and 4,528,180 to Schaeffer. Carriers suitable for the preparation of compositions of the present invention are well known in the art. Their selection will depend on secondary considerations like taste, cost, and shelf stability, etc.

The compositions of the present invention may be in the form of non-abrasive gels, including subgingival gels, which may be aqueous or non-aqueous. Aqueous gels generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), and the balance water. The compositions may comprise an anticaries agent (from about 0.05% to about 0.3% as fluoride ion), and an anticalculus agent (from about 0.1% to about 13%).

Compositions of the subject invention may also be in the form of dentifrices, such as toothpastes, tooth gels and tooth powders. Components of such toothpaste and tooth gels generally include one or more of a dental abrasive (from about 5% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion), and an anticalculus agent (from about 0.1% to about 13%). Tooth powders, of course, contain substantially all non-liquid components.

Other preferred compositions of the subject invention are mouthwashes, including mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion), and an anticalculus agent (from about 0.1% to about 3%).

Other preferred compositions of the subject invention are dental solutions including irrigation fluids. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of a gum base (from about 50% to about 99%), a flavoring agent (from about 0.4% to about 2%) and a sweetening agent (from about 0.01% to about 20%).

The term "lozenge" as used herein includes: breath mints, troches, pastilles, microcapsules, and fast-dissolving solid forms including freeze dried forms (cakes, wafers, thin films, tablets) and compressed tablets. The term "fast-dissolving solid form" as used herein means that the solid dosage form dissolves in less than about 60 seconds, preferably less than about 15 seconds, more preferably less than about 5 seconds, after placing the solid dosage form in the oral cavity. Fast-dissolving solid forms are disclosed in commonly-assigned WO 95/33446 and WO 95/11671; U.S. Pat. Nos. 4,642,903; 4,946,684; 4,305,502; 4,371,516; 5,188,825; 5,215,756; 5,298,261; 3,882,228; 4,687,662; 4,642,903.

Lozenges include discoid-shaped solids comprising a therapeutic agent in a flavored base. The base may be a hard sugar candy, glycerinated gelatin or combination of sugar with sufficient mucilage to give it form. These dosage forms are generally described in Remington: *The Science and Practice of Pharmacy*, 19$^{th}$ Ed., Vol. II, Chapter 92, 1995. Lozenge compositions (compressed tablet type) typically include one or more fillers (compressible sugar), flavoring agents, and lubricants. Microcapsules of the type contemplated herein are disclosed in U.S. Pat. No. 5,370,864, Peterson et al., issued Dec. 6, 1994.

In still another aspect, the invention provides a dental implement impregnated with the present composition. The dental implement comprises an implement for contact with teeth and other tissues in the oral cavity, said implement being impregnated with a composition comprising the present dicarboxy functionalized siloxane polymer. The dental implement can be impregnated fibers including dental floss or tape, chips, strips, films and polymer fibers.

Types of carriers or oral care excipients, which may be included in compositions of the present invention, along with specific non-limiting examples, are the following.

Abrasives

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resin as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, Zeodent®, particularly the silicas carrying the designation Zeodent® 119, Zeodent® 118, Zeodent® 128, Zeodent® 109 and Zeodent® 129. The types of silica dental abrasives useful in the toothpastes of the present invention are described in more detail in Wason, U.S. Pat. No. 4,340,583, issued Jul. 29, 1982; and in commonly-assigned U.S. Pat. No. 5,603,920, issued on Feb. 18, 1997; U.S. Pat. No. 5,589,160, issued Dec. 31, 1996; U.S. Pat. No. 5,658,553, issued Aug. 19, 1997; U.S. Pat. No. 5,651,958, issued Jul. 29, 1997; U.S. Pat. No. 5,716,601, issued Feb. 10, 1998 and U.S. Provisional Application Ser. No. 60/300,766, filed Jun. 25, 2001.

Mixtures of abrasives can be used. The total amount of abrasive in dentifrice compositions of the subject invention preferably range from about 6% to about 70% by weight; toothpastes preferably contain from about 10% to about 50% of abrasives, by weight of the composition. Solution, mouth spray, mouthwash and non-abrasive gel compositions of the subject invention typically contain no abrasive.

Surfactants

One of the optional agents of the present invention is a surfactant, preferably one selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate.

This surfactant can be present in the compositions of the present invention from about 0.1% to about 2.5%, preferably from about 0.3% to about 2.5% and most preferably from about 0.5% to about 2.0% by weight of the total composition.

Other suitable compatible surfactants can optionally be used or in combination with the sarcosinate surfactant in the compositions of the present invention. Suitable optional surfactants are described more fully in U.S. Pat. No. 3,959,458, May 25, 1976 to Agricola et al.; U.S. Pat. No. 3,937,807, Feb. 10, 1976 to Haefele; and U.S. Pat. No. 4,051,234, Sep. 27, 1988 to Gieske et al.

Preferred anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be utilized.

Preferred cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., where said quaternary ammonium fluorides have detergent properties. Certain cationic surfactants can also act as germicides in the compositions disclosed herein. Cationic surfactants such as chlorhexidine, although suitable for use in the current invention, are not preferred due to their capacity to stain the oral cavity's hard tissues. Persons skilled in the art are aware of this possibility and should incorporate cationic surfactants only with this limitation in mind.

Preferred nonionic surfactants that can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic synthetic surfactants useful in the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Preferred betaine surfactants are disclosed in U.S. Pat. No. 5,180,577 to Poleflka et al., issued Jan. 19, 1993. Typical alkyl dimethyl betaines include decyl betaine or 2-(N-decyl-N,N-dimethylammonio)acetate, coco betaine or 2-(N-coco-N,N-dimethyl ammonio)acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramidopropyl betaine.

Anticalculus Agent

The present compositions may also include an anticalculus agent, preferably synthetic anionic polymers, including polyacrylates and copolymers of maleic anhydride or acid and methyl vinyl ether (e.g., Gantrez), as described, for example, in U.S. Pat. No. 4,627,977, to Gaffar et al.; as well as, e.g., polyamino propane sulfonic acid (AMPS), zinc citrate trihydrate, polypeptides (such as polyaspartic and polyglutamic acids), and mixtures thereof.

Chelating Agents

Another preferred optional agent is a chelating agent such as tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention.

Sodium and potassium citrate are the preferred alkali metal citrates, with sodium citrate being the most preferred. Also preferred is a citric acid/alkali metal citrate combination. Preferred herein are alkali metal salts of tartaric acid. Most preferred for use herein are disodium tartrate, dipotassium tartrate, sodium potassium tartrate, sodium hydrogen tartrate and potassium hydrogen tartrate. The amounts of chelating agent suitable for use in the present invention are about 0.1% to about 2.5%, preferably from about 0.5% to about 2.5% and more preferably from about 1.0% to about 2.5%. The tartaric acid salt chelating agent can be used alone or in combination with other optional chelating agents. Preferably these chelating agents have a calcium binding constant of about $10^1$ to $10^5$ to provide improved cleaning with reduced plaque and calculus formation.

Still another possible group of chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having an average molecular weight (AMW) of about 30,000 to about 1,000,000. These copolymers are available for example as Gantrez AN 139 (AMW 500,000), AN 119 (AMW 250,000) and preferably S-97 Pharmaceutical Grade (AMW 70,000), of GAF Chemicals Corporation.

Other operative polymeric polycarboxylates include those such as the 1:1 copolymers of maleic anhydride with ethyl acrylate, hydroxyethyl methacrylate, N-vinyl-2-pyrrolidone, or ethylene, the latter being available for example as Monsanto EMA No. 1103, AMW 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether, polyacrylic, polyitaconic and polymaleic acids, and sulfoacrylic oligomers of AMW as low as 1,000 available as Uniroyal ND-2.

Fluoride Source

It is common to have an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al. Representative fluoride ion sources include stannous fluoride, sodium fluoride, potassium fluoride, sodium monofluorophosphate and many others. Stannous fluoride and sodium fluoride are particularly preferred, as well as mixtures thereof.

Teeth Whitening Actives and Teeth Color Modifying Substances

In addition to bleaching agents as teeth whitening agents, teeth color modifying substances may be considered among the oral care actives useful in the present invention. These substances are suitable for modifying the color of the teeth to satisfy the consumer. These substances comprise particles that when applied on the tooth surface modify that surface in terms of absorption and, or reflection of light. Such particles provide an appearance benefit when a film containing such particles is applied over the surfaces of a tooth or teeth.

Particles most useful in the present invention include pigments and colorants routinely used in the cosmetic arts. There are no specific limitations as to the pigment and, or colorant used in the present composition other than the limitation of the effect it has on the light source upon the teeth surfaces. Pigments and colorants include inorganic white pigments, inorganic colored pigments, pearling agents, filler powders and the like; see Japanese Published Patent Application Kokai No. 9-100215, published Apr. 15, 1997. Specific examples are selected from the group consisting of talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Most preferred are those selected from the group consisting of titanium dioxide, bismuth oxychloride, zinc oxide and mixtures thereof. Pigments that are generally recognized as safe, and are listed in C.T.F.A. Cosmetic Ingredient Handbook, 3rd Ed., Cosmetic and Fragrance Assn., Inc., Washington D.C. (1982).

The pigments are typically used as opacifiers and colorants. These pigments can be used as treated particles, or as the raw pigments themselves. Typical pigment levels are selected for the particular impact that is desired by the consumer. For example, for teeth that are particularly dark or stained one would typically use pigments in sufficient amount to lighten the teeth. On the other hand, where individual teeth or spots on the teeth are lighter than other teeth, pigments to darken the teeth may be useful. The levels of pigments and colorants are generally used in the range of about 0.05% to about 20%, preferably from about 0.10% to about 15% and most preferably from about 0.25% to about 10% of the composition.

Thickening Agents

In preparing toothpaste or gels, it is necessary to add some thickening material to provide a desirable consistency of the composition, to provide desirable active release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

A preferred class of thickening or gelling agents includes a class of homopolymers of acrylic acid crosslinked with an alkyl ether of pentaerythritol or an alkyl ether of sucrose, or carbomers. Carbomers are commercially available from B.F. Goodrich as the Carbopol® series. Particularly preferred Carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. No. 5,198,220, issued Mar. 30, 1993 and U.S. Pat. No. 5,242,910, issued Sep. 7, 1993, both to Damani, and U.S. Pat. No. 4,443,430, to Mattei, issued Apr. 17, 1984.

Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges (including breath mints), sachets, non-abrasive gels and subgingival gels.

Humectants

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and Sweetening Agents

Flavoring agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Preferred salivating agents of the present invention include Jambu® manufactured by Takasago. Preferred warming agents include capsicum and nicotinate esters, such as benzyl nicotinate. Preferred numbing agents include benzocaine, lidocaine, clove bud oil, and ethanol.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Miscellaneous Carriers

Water employed in the preparation of commercially suitable oral compositions should preferably be of low ion content and free of organic impurities. Water generally comprises from about 5% to about 70%, and preferably from about 20% to about 50%, by weight of the aqueous compositions herein. These amounts of water include the free water which is added plus that which is introduced with other materials, such as with sorbitol.

Poloxamers may be employed in the present compositions. A poloxamer is classified as a nonionic surfactant. It may also function as an emulsifying agent, binder, stabilizer, and other related functions. Poloxamers are difunctional block-polymers terminating in primary hydroxyl groups with molecular weights ranging from 1,000 to above 15,000. Poloxamers are sold under the tradename of Pluronics and Pluraflo by BASF. Preferred poloxamers for this invention are Poloxamer 407 and Pluraflo L4370.

Other emulsifying agents that may be used in the present compositions include polymeric emulsifiers such as the Pemulen® series available from B.F. Goodrich, and which are predominantly high molecular weight polyacrylic acid polymers useful as emulsifiers for hydrophobic substances.

Titanium dioxide may also be added to the present composition. Titanium dioxide is a white powder which adds opacity to the compositions. Titanium dioxide generally comprises from about 0.25% to about 5% by weight of the dentifrice compositions.

The pH of the present compositions is preferably adjusted through the use of buffering agents. Buffering agents, as used herein, refer to agents that can be used to adjust the pH of the compositions to a range of about pH 4.0 to about pH 10.0. Buffering agents include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions. The pH of dentifrice compositions is measured from a 3:1 aqueous slurry of dentifrice, e.g., 3 parts water to 1 part dentifrice.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the Trade Name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits.

Other Active Agents

The present oral compositions may also include other active agents, such as antimicrobial agents. Included among such agents are water insoluble non-cationic antimicrobial agents such as halogenated diphenyl ethers, phenolic compounds including phenol and its homologs, mono and polyalkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquamide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethyl-hexyl)-5-methyl-hexahydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. Pat. No. 4,206,215, issued Jun. 3, 1980, to Bailey. Other antimicrobials such as copper bisglycinate, copper glycinate, zinc citrate, and zinc lactate may also be included. Enzymes are another type of active that may be used in the present compositions. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranases, mutanases; and oxidases include glucose oxidase, lactate oxidase, galactose oxidase, uric acid oxidase, peroxidases including horse radish peroxidase, myeloperoxidase, lactoperoxidase, chloroperoxidase. The oxidases also have whitening/cleaning activity, in addition to antimicrobial properties. Such agents are disclosed in U.S. Pat. No. 2,946,725, Jul. 26, 1960, to Norris et al. and in U.S. Pat. No. 4,051,234, Sep. 27, 1977 to Gieske et al. Other antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. These agents, which provide anti-plaque benefits, may be present at levels of from about 0.01% to about 5.0%, by weight of the dentifrice composition.

Method of Use

The present invention also relates to methods for cleaning and polishing teeth and reducing the incidence of stain, plaque, gingivitis and calculus on dental enamel.

The method of use herein comprises contacting a subject's dental enamel surfaces and oral mucosa with the oral compositions according to the present invention. The method of use may be by brushing with a dentifrice, rinsing with a dentifrice slurry or mouthrinse, or chewing a gum product. Other methods include contacting the topical oral gel, mouthspray, or other form such as strips or films with the subject's teeth and oral mucosa. The composition may be applied directly to the teeth, gums, or other oral surface with a brush, a pen applicator, a doe's foot applicator, or the like, or even with the fingers. The subject may be any person or other animal whose tooth surface contacts the oral composition. By "other animal" is meant to include household pets or other domestic animals, or animals kept in captivity. For example, a method of use may include brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions. The composition including the present copolymer is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope. All percentages used herein are by weight of the composition unless otherwise indicated.

Example 1

Preparation of a Dicarboxy Functionalized Polydimethylsiloxane Having Pendant —(CH$_2$)$_3$—CH(COOH)—CH$_2$COOH Groups 93.7 g (i.e., 0.67 mol) of allyl succinic anhydride, 52 g of toluene and 1.01 g of a Kardtedt catalyst solution (0.1% of Pt in hexamethyldisiloxane) are added into a 500 ml reactor. The reaction mass is heated at 90° C.; 120 g (i.e., 0.45 mol of SiH) of a polydimethylhydrogenosiloxane having the formula

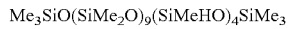

and containing 3.75 mol of SiH/kg, are added over 3 hours. The SiH amount (determined by gazometry) transformed at the end of the addition is of 96.1%; it is of 100% 2 hours after the end of the addition. The volatiles are eliminated by evaporation under vacuum (3 mbar) over 10 hours at 150° C. 15 g of demineralized water are then added in order to hydrolyze the succinic anhydride functions. The hydrolysis reaction is followed by infra-red analysis (acid band at 1714 cm$^{-1}$, anhydride band at 1863 and 1782 cm$^{-1}$). When the hydrolysis reaction is complete (48 hours), 100 g of toluene are added in order to azeotropically eliminate water. 133.5 g (corresponding to a yield of 82%) of a viscous oil are recovered.

NMR analysis confirmed the following general structure of the product obtained:

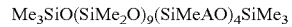

in which A represents —(CH$_2$)$_3$—CH(COOH)—CH$_2$COOH.

Example 2

Preparation of a Dicarboxy Functionalized Polydimethylsiloxane Having Pendant —(CH$_2$)$_3$—CH(COOH)—CH$_2$COOH Groups 49.8 g (i.e., 0.36 mol) of allyl succinic anhydride, 44 g of toluene and 1.139 g of a Kardtedt catalyst solution (0.1% of Pt in hexamethyldisiloxane) are added into a 500 ml reactor. The reaction mass is heated at 90° C.; 150.3 g (i.e., 0.266 mol of SiH) of a polydimethylhydrogenosiloxane having the formula

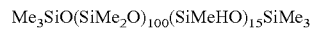

and containing 1.77 mol of SiH/kg, are added over 1 hour. The SiH amount (determined by gazometry) transformed at the end of the addition is of 86%; it is of 100% 16 hours after the end of the addition. The volatiles are eliminated by evaporation under vacuum (6 mbar) over 10 hours at 150° C. 101 g of toluene are added; the reaction mass is filtered. 6.7 g of demineralized water are then added in order to hydrolyze the succinic anhydride functions. The hydrolysis reaction is followed by infrared analysis (acid band at 1714 cm$^{-1}$, anhydride band at 1866 and 1788 cm$^{-1}$). When the hydrolysis reaction is complete (6 days), water is azeotropically eliminated. 146.3 g (corresponding to a yield of 80%) of a viscous oil are recovered.

NMR analysis confirmed the following general structure of the product obtained:

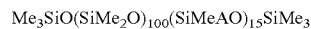

in which A represents —(CH$_2$)$_3$—CH(COOH)—CH$_2$COOH

Example 3

Retention of Functionalized Siloxane Polymers Applied as a 1% Solution on Polished Bovine Enamel Surfaces The deposition and retention of dicarboxy functionalized siloxane polymers according to the present invention applied as a 1% solution on polished bovine enamel surfaces are compared with other siloxane polymers containing other functional groups. Solutions of the different siloxane polymers were prepared at 1% concentration in MIBK (methyl isobutyl ketone). Six □l of each solution was applied directly to clean, polished bovine enamel specimens set in resin, having approximately 1 cm$^2$ surface area. The solvent was allowed to evaporate under ambient conditions and an initial water contact angle (WCA) was measured using a Kruss DSA-10 system. The enamel specimens were then soaked in ultra pure water for 5 minutes, and after allowing to air dry the water contact angle was re-measured. Then, the specimens were brushed on a brushing machine (V-8 crossover with an Oral-B flat head toothbrush at 150 g pressure) for 1 minute and 10 minutes with water, and the WCA's re-measured at each interval. Untreated enamel specimens were included in this study as a control. The results are summarized in Table I below. The siloxane polymers functionalized with acid anhydride and its hydrolyzed diacid show the best retention properties in the bovine enamel brushing model as demonstrated by the relatively higher WCA values indicating a more hydrophobic surface, which are maintained even after brushing for 10 minutes.

TABLE I

Water Contact Angles of Bovine Enamel Surfaces Treated With Functionalized Siloxane Polymers

| Functional group of Siloxane Polymer | Average MW | WCA After Treatment | 5 min H2O soak | 1 min brushing | 10 min brushing |
|---|---|---|---|---|---|
| Polyether | 15000 | 25.70 | 34.35 | 35.32 | |
| Amine | 17000 | 65.86 | 61.12 | 54.56 | |
| Polyether/polyol | 14000 | 83.19 | 85.01 | 51.68 | |
| Propylsuccinic Anhydride | 1600 | 92.31 | 90.00 | 91.46 | 92.51 |
| Propylsuccinic Anhydride | 360 | 93.96 | 92.15 | 86.52 | 65.28 |
| Propylsuccinic acid | 10000 | 86.38 | 96.83 | 83.08 | 84.75 |
| Propylsuccinic acid | 1700 | 28.19 | 70.34 | 82.9 | 86.53 |
| Enamel control | | 48.39 | 50.75 | 42.97 | 54.86 |

Example 4

Deposition and Retention of Functionalized Siloxane Polymers Applied as a 1% Concentration Dentifrice Slurry Brushed onto Polished Bovine Enamel Functionalized siloxane polymers were mixed with Crest® cavity fighting formula dentifrice and water (1:3) to give a dentifrice slurry containing each polymer at 1% concentration in the slurry. Clean, polished bovine enamel specimens set in resin and having approximately 1 cm$^2$ surface area were dropped into each slurry to soak for 5 minutes. Specimens were removed, then sonicated and rinsed in ultrapure water. They were then air dried, and a water contact angle (WCA) measurement was made on the enamel surface. Specimens were mounted on a brushing machine (V-8 crossover with an Oral-B flat head toothbrush at 150 g pressure) and brushed with prepared slurries for 1 minute and 10 minutes. WCA's were re-measured after each interval using the same method described. Untreated enamel specimens were included in this study as a control. Results are shown in the Table II below. The diacid functionalized siloxane polymers according to the present invention were deposited and retained on enamel better than the other functionalized siloxane polymers tested, with the propylsuccinic acid functionalized polymer (AMW=1700) having the best deposition and retention. The anhydride functionalized polymer also maintained a hydrophobic surface as indicated by the relatively higher WCA values, although the hydrophobicity was not retained as well as with the diacid functionalized polymers. The copolyol functionalized polymer had little retention on enamel under these brushing conditions.

TABLE II

Water Contact Angles of Bovine Enamel Surfaces Treated With Functionalized Siloxane Polymers Incorporated in a Dentifrice

| | | Water Contact Angle Measurements | | |
|---|---|---|---|---|
| Functional group | AMW | 5 min soak | 1 min brushing | 10 min brushing |
| Propylsuccinic acid | 1700 | 82.33 | 98.85 | 98.77 |
| Propylsuccinic acid | 10000 | 53.19 | 55.87 | 49.77 |
| Propylsuccinic Anhydride | 1600 | 84.0 | 70.0 | 68.0 |
| Polyol/polyether | 14000 | 57.0 | 25.0 | 25.0 |
| Bare enamel control | | 26.0 | 25.0 | 25.0 |

Example 5

Bleaching Performance of a Mixture of a Propylsuccinic Acid Functionalized Siloxane Polymer and Carbamide Peroxide (CP) Against Extrinsic Stains on Bovine Enamel The bleaching performance against extrinsic stains of a composition according to the present invention comprising a diacid functionalized siloxane polymer and 10% carbamide peroxide is compared to performance of compositions comprising a Carbopol gel or water and the same level of carbamide peroxide. Bovine enamel specimens were mounted in a resin, and exposed to a staining solution to induce a dark stain on the enamel surface. Baseline CIE (International Commission of Illumination) L*a*b* values were measured using a Fuji HC1000 digital camera under controlled lighting conditions (D55 light) with a polarizing filter. Carbamide peroxide (urea hydrogen peroxide, Sigma U-1753) was mixed into the following test materials at a 10% concentration: propylsuccinic acid functionalized siloxane polymer (AMW=1700); 5% Carbopol gel; and ultrapure water. Approximately 10 mg of each test material mixture was applied to the enamel surface of the bovine specimens, and the specimens were then placed into individual vials containing 15 mL of ultrapure water, and the vials were then placed on a rocker, in an incubator set at 37° C. for 30 minutes. At the end of 30 minutes, the treatments were removed by gently swabbing the surface with MIBK. The specimens were blotted dry and measured for changes in L*, a*, and b*, a numerical expression of three dimensional color space where L* represents lightness on the y axis, a* represents chroma (red-green) on the x axis, and b* represents chroma (yellow-blue) on the z axis. Subsequent treatments were then applied the same way, and this procedure was repeated for 14 treatments, for a total exposure time of 7 hours. Condensed results are shown in Table III below as change in delta L* vs. baseline. The diacid functionalized siloxane polymer provides an enhanced bleaching benefit on extrinsic stain versus Carbopol gel or water containing the same concentration of carbamide peroxide under aqueous conditions.

TABLE III

ΔL* vs. Baseline of Extrinsically Stained Bovine Enamel

| Treatment | Treatment Time | | | |
|---|---|---|---|---|
| | 1 hr | 3 hrs | 5 hrs | 7 hrs |
| Propylsuccinic Acid Functionalized Siloxane Polymer + 10% CP | 3.5 | 12 | 22 | 29 |
| Carbopol gel + 10% CP | 0 | 5 | 9 | 12 |
| Ultrapure water + 10% CP | 0 | 1 | 3 | 5 |

Example 6

Bleaching of Intrinsically Discolored Extracted Human Teeth Following Brushing with a Dentifrice Containing a Propylsuccinic Acid Functionalized Siloxane Polymer and Carbamide Peroxide (CP)

Extracted human molars were cleaned of any soft tissue, and polished/prophied to remove any tartar or extrinsic stains. They were mounted in a resin and baseline CIE L*a*b* values were measured using a Fuji HC1000 digital camera under controlled lighting conditions (D55 light) with a polarizing filter. Carbamide peroxide (urea hydrogen peroxide, Sigma U-1753) was added to a methyl isobutyl ketone (MIBK) solution containing dissolved propylsuccinic acid functionalized siloxane polymer (AMW=1700). The solvent was evaporated off and the residue of CP/polymer was then added to a slurry of Crest cavity protection dentifrice so that the resulting slurry contained 10% CP and 5% polymer. A comparative slurry containing only 10% CP was also made. An Oral B flathead toothbrush was dipped into the slurry, and the slurry brushed onto one side of the molar for 50 hand strokes. This was repeated for all sides of the tooth (buccal, lingual distal and labial sides each received 50 strokes). The specimens were then placed into individual vials containing 15 mL of ultrapure water, and the vials were then placed on a rocker, in an incubator set at 37° C. for 1 hour. At the end of 1 hour, the treatments were removed by gently swabbing the surface with MIBK. Specimens receiving the comparative slurry were treated the same way. The teeth were lightly blotted dry and measured for changes in L*, a*, b* color space. Subsequent treatments were then applied the same way, and this procedure was repeated for a total exposure time of 7 hours. Results are shown in Table IV below as change in delta L* vs. baseline. These results demonstrate that the present composition comprising the diacid functionalized siloxane polymer, provides significantly greater bleaching benefit on intrinsic discolorations/stains of extracted human teeth versus carbamide peroxide alone when delivered to the tooth surface from a dentifrice slurry aids in the retention of carbamide peroxide on the tooth surface. The results further demonstrate that the diacid functionalized siloxane polymer aids in the retention of carbamide peroxide on the tooth surface resulting in greater bleaching effect over time.

TABLE IV

ΔL* vs. Baseline of Intrinsically Stained Human Enamel

| Treatment | Treatment Time | | | |
|---|---|---|---|---|
| | 1 hr | 3 hrs | 5 hrs | 7 hrs |
| 5% Propylsuccinic Acid Siloxane Polymer (AMW = 1700) + 10% CP | 1 | 2 | 3 | 4 |
| 10% CP | 0.5 | 1 | 1 | 1 |

Example 7

Topical Oral Gels

Topical oral gels according to the present invention are shown below. These compositions are made using conventional methods.

| Components | 7A | 7B | 7C | 7D | 7E | 7F | 7G |
|---|---|---|---|---|---|---|---|
| Flavor | 5.000 | 5.000 | 0.500 | 0.500 | 0.500 | 0.500 | 0.500 |
| Menthol | 0.200 | 0.200 | | | | | |
| Saccharin | 0.200 | 0.200 | 0.100 | 0.100 | 0.100 | 0.100 | 0.100 |
| Propylsuccinic Acid Polysiloxane Polymer (AMW = 1700 or 10000) | 3.000 | 3.000 | 70.000 | 75.000 | 66.000 | 80.000 | 75.00 |
| Urea Peroxide | 10.000 | | 20.000 | 15.000 | 15.000 | | |
| Triclosan | | | | | | 0.300 | |
| Cetyl Pyridinium Chloride | | | | | | | 1.00 |
| Pemulen TR1 | 1.000 | 1.000 | | | | | |
| Dibasic Na Phosphate | 0.200 | 0.200 | | | | | |
| Poloxamer 407 | 9.000 | 10.500 | | | | | |
| Pluraflo L4370 | QS | QS | | | | | |
| PEG 600 | | | QS | QS | QS | QS | QS |

Example 8

Dentifrice Compositions

Dentifrice compositions according to the present invention are shown below. These compositions are made using conventional methods.

| Components | 8A | 8B | 8C | 8D | 8E | 8F |
|---|---|---|---|---|---|---|
| Color FD&C Blue#1 | | 0.300 | | | 0.200 | 0.200 |
| Carbomer 956 | 2.000 | | | 2.000 | 0.300 | 0.300 |
| Citric Acid | | | 0.180 | | | |
| Flavor | 0.900 | 1.100 | 1.000 | 0.900 | 1.200 | 0.800 |
| Saccharin | 0.300 | 0.400 | 0.450 | 0.400 | 0.300 | 0.350 |
| Glycerin | 10.000 | 30.000 | 30.000 | QS | | |
| Monosodium Phosphate | | 0.500 | | | 0.590 | 0.500 |
| Trisodium Phosphate | | | | | 1.450 | 1.400 |
| Xanthan Gum | | | | | 0.475 | 0.500 |
| Na Hydroxide (50% soln) | 1.100 | | | | | |
| PEG 40 SDIS | | | 1.240 | | | |
| Poloxamer 407, NF | | 15.000 | 15.000 | 5.000 | | |
| Powdered Polyethylene | | 20.000 | 15.430 | | | |
| Silica | | | | 10.000 | 20.000 | 15.000 |
| Sodium Stannate | | | 0.090 | | | |
| Sodium Fluoride | 0.243 | 0.243 | 0.243 | 0.243 | 0.243 | 0.243 |
| Sorbitol (70% soln) | | | | | 50.000 | 40.000 |
| Sodium Alkyl Sulfate (28% soln) | 3.000 | | | | 4.000 | 5.000 |
| Propylsuccinic Acid Polysiloxane Polymer | | 5.000 | | 3.000 | | 1.000 |
| Propylsuccinic Acid/Propylene Glycol ester Polysiloxane Polymer | 3.000 | | 2.000 | | 4.000 | |
| Urea Peroxide | 10.000 | | | 4.000 | | |
| Hydrogen Peroxide (35% soln) | | 5.000 | 3.000 | | | |
| Triclosan | 0.300 | | | | 0.300 | |
| Cetyl Pyridinium Chloride | | | 0.530 | | | |
| Vitamin E | | | | | | 2.000 |
| Water, Purified USP | QS | QS | QS | | QS | QS |

Example 9

Chewing Gum Compositions

Chewing gum compositions including a coated chewing gum (9C) according to the present invention are shown below.

| Components | 9A | 9B |
|---|---|---|
| Xylitol | 16.700 | 16.700 |
| Gum base (e.g., Prestige-PL, Cafosa) | 28.000 | 28.000 |
| Propylsuccinic Acid Functionalized Polysiloxane (AMW = 1700) | 5.000 | 5.000 |
| Urea Hydrogen Peroxide | | 10.000 |
| Hydrogenated starch hydrolysate (85% solids) | 8.000 | 8.000 |
| Glycerin | 7.000 | 7.000 |
| Mannitol | 5.000 | 5.000 |
| Flavor | 1.600 | 1.600 |
| Aspartame | 0.200 | 0.200 |
| Spray dried menthol | 0.150 | 0.150 |
| Sorbitol | QS | QS |

| 9C Components | Core 1 g/piece | Coating 0.35 g/piece | Total 1.35 g/piece |
|---|---|---|---|
| Sorbitol | 49.35 | — | 36.56 |
| Gum base[1] | 25.0 | — | 18.52 |
| Propylsuccinic Acid Functionalized Siloxane Polymer (AMW = 1700) | 5.0 | | 3.70 |
| Urea Hydrogen Peroxide | 5.0 | — | 3.70 |
| Sodium fluoride | — | 0.08 | 0.02 |
| Xylitol | — | — | — |
| Hydrogenated Starch Hydrolysate | 5.0 | — | 3.70 |
| Mannitol | 2.0 | — | 1.48 |
| Glycerin | 5.0 | — | 3.70 |
| Titanium dioxide | — | 2.0 | 0.52 |
| Flavor | 2.0 | 2.0 | 2.00 |
| Additional spray-dried flavor | 1.5 | — | 1.11 |
| Sucralose | 0.05 | 0.03 | 0.05 |
| Potassium Acesulfame | 0.10 | 0.10 | 0.10 |
| Sorbitol[2] | — | 95.25 | 24.70 |
| Polysorbate 60 | — | 0.30 | 0.08 |
| Insoluble edible glitter[3] (Brilliant Blue) | — | 0.04 | 0.01 |
| Wax[4] | — | 0.20 | 0.05 |

Making Instructions

Example 9A and 9B

Heat gum base to ~45° C. to soften. Maintain mixer vessel cavity at ~45° C. during entire mixing process. Add gum base to mixing cavity of double sigma blade mixer and mix for 5 minutes. Add mannitol and spray-dried menthol. Mix for 2 minutes. Add glycerin and mix for 2 minutes. Add 50% of xylitol and mix for 2 minutes. Add hydrogenated starch hydrolysate and mix for 5 minutes. Add 50% sorbitol and mix for 3 minutes. Add second 50% of xylitol, silicone, and aspartame and mix for 3 minutes. Add flavor and mix for 3 minutes. In the case of Ex. 9B, add the bleach toward the end at close to room temperature to minimize active oxygen loss.

Making Instructions

Example 9C

Core Formulation: Soften gum base with gentle heating and add mannitol, spray-dried flavor, glycerin, 50% of xylitol, hydrogenated starch hydrolysate, 50% of sorbitol and mix thoroughly. Add second 50% of xylitol, siloxane polymer and urea hydrogen peroxide (when needed) and aspartame, remainder of flavor and mix further. Form bulk chewing gum mass into discrete pieces of desired shape and size using rolling and scoring equipment.

Coating Solution: Add titanium dioxide and Polysorbate 60 to 70% aqueous sorbitol solution and mix. Add flavor followed by Sucralose and Potassium Acesulfame and mix further.

Coating of Core Formulation: Place gum pieces into a coating pan and apply coating solution, partially dry. Repeat coating step until desired coating thickness or weight is achieved. Apply clear 70% aqueous sorbitol solution and, whilst wet, dry spray speckles onto product surface, dry. Apply second coat of clear 70% sorbitol solution followed by wax coating and allow product to fully dry.

Example 10

Mouthrinse

| Components | Weight % |
| --- | --- |
| Water | 29.000 |
| Propylene Glycol | 53.459 |
| Sodium Benzoate | 0.320 |
| Benzoic Acid | 0.021 |
| Sodium Saccharin | 0.700 |
| Propylsuccinic Acid Functionalized Polysiloxane (AMW = 1700) | 5.000 |
| Poloxamer 407 | 10.000 |
| Flavor | 1.500 |

Example 10 mouthrinse is prepared as follows: Mix water, poloxamer and propylene glycol. Next add the flavor, benzoic acid, and the siloxane polymer. Finally add the sodium benzoate and sodium saccharin and mix until homogeneous.

Example 11

Denture Adhesive Compositions

Denture adhesive compositions in cream form can be made by blending together the following components.

| Components | 11A | 11B | 11C | 11D |
| --- | --- | --- | --- | --- |
| White Mineral Oil | 23.93 | 23.93 | 23.93 | 0 |
| Petrolatum, White | 21.77 | 20.87 | 11.87 | 0 |
| Carboxymethylcellulose Sodium | 20.00 | 20.00 | 20.00 | 20.00 |
| Silicon Dioxide, Colloidal | 1.14 | 1.14 | 1.14 | 1.14 |
| Colorant (Opatint Red Dye) | 0.06 | 0.06 | 0.06 | 0.06 |
| Propylsuccinic Acid Functionalized Polysiloxane (AMW = 1700) | 0.10 | 1.00 | 10.00 | 45.8 |
| Alkyl Vinyl Ether/Maleic Acid (AVE/MA) Copolymer Salt | 33.00 | 33.00 | 33.00 | 33.00 |

Mix the fluid components (red dye, Propylsuccinic Acid Polysiloxane, petrolatum, mineral oil) at 50 to 60° C. until visually uniform. Then shake-blend the powder components (colloidal silicon dioxide, CMC, any AVE/MA copolymer mixed salt) together in a container. Thereafter, mix the powders into the liquid forming a uniform pink cream. The cream compositions may be modified by increasing or decreasing the levels of each of the AVE/MA salt of, petrolatum, and/or the CMC by up to 10 grams. The above cream compositions can also be modified by using mixtures of various AVE/MA mixed polymer salts, such as Ca/Zn or Mg/Ca/Zn salts, and/or acid. In use the subject places from 0.1 to 2 grams of the cream composition on the denture. Then the subject inserts the denture into his/her mouth and presses it into place.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising
   (a) an orally acceptable carrier;
   (b) at least one oral care agent suitable for administration to a subject's oral cavity, selected from the group consisting of a bleaching agent, teeth color modifying agent, enzyme, anti-tartar agent, fluoride ion source, anti-microbial agent, anti-inflammatory agent, H2 antagonist, analgesic, anti-viral agent, denture adhesive, flavoring agent, abrasive, desensitizing agent, anticaries agent, chelating agent and mixtures thereof; and
   (c) at least about 0.1% by weight of a dicarboxy functionalized siloxane polymer of formula

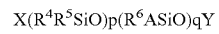

wherein
   X represents a triorganosiloxyl end group of formula $R^1R^2R^3SiO—$, or a Z end group wherein Z represents —OH;
   Y represents a triorganosilyl end group of formula $—SiR^3R^2R^1$ or a W end group wherein W is hydrogen;
   $R^1$ to $R^6$, which may be identical or different, each represents a linear or branched C1–C8 alkyl or a phenyl radical;
   A represents a dicarboxy acid radical of formula

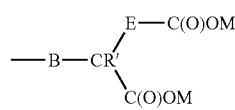

wherein
   B represents an alkylene residue having from 2 to 30 carbon atoms, optionally substituted by one or more alkyl radicals having from 1 to 30 carbon atoms,
   R' represents a hydrogen atom or an alkyl radical having from 1 to 30 carbon atoms, E is nil or is an alkylene residue having from 1 to 5 carbon atoms, optionally substituted by one or more alkyl radicals having from 1 to 30 carbon atoms; and M is H, an alkyl group having from 1 to 4 carbon atoms optionally substituted with hydroxy or alkoxy groups, or a cation selected from the group consisting of alkali metal, alkaline earth metal, and substituted or non substituted ammonium, piperidinium or alkanolamine;

p is an average value ranging from 0 to 1000;

q is an average value ranging from 1 to 100; and the ratio of the number of Z and W end groups to the total number of X and Y end groups is from 0/100 to 75/100, wherein the oral care composition is in a form selected from a dentifrice, toothpaste, tooth powder, topical oral gel, mouthrinse, dental solution, denture product, mouthspray, lozenge, oral tablet, chewing gum and impregnated dental implement or pet chew.

2. An oral care composition according to claim 1 wherein the dicarboxy functionalized siloxane polymer comprises one or a combination of dicarboxy acid pendant groups selected from:

wherein n is from 2 to 30.

3. An oral care composition according to claim 1 wherein the oral care agent is a bleaching agent in an amount from about 0.1% in about 20.0% by weight of the composition.

4. An oral care composition according to claim 3 wherein the bleaching agent is selected from the group consisting of peroxides, perborates, percarbonates, peroxyacids, persulfates, chlorites, and mixtures thereof.

5. An oral care composition according to claim 4 wherein the bleaching agent is selected from the group consisting of hydrogen peroxide, urea peroxide, calcium peroxide, sodium percarbonate, sodium chlorite, potassium chlorite and mixtures thereof.

6. A method of cleaning and whitening a subject's teeth or dental prosthesis; preventing or reducing plaque, caries, calculus and tooth stains; and providing shine, smoothness and positive feel benefits to teeth comprising administering a composition according to claim 1.

7. A method of enhancing efficacy of oral care compositions comprising including in said compositions a carrier for oral care active agents comprising a dicarboxy functionalized siloxane polymer in an amount effective to hydrophobically modify teeth and other oral surfaces and to enhance delivery and retention of said active agents on teeth and other oral surfaces.

* * * * *